United States Patent
Jamison et al.

(10) Patent No.: US 10,209,169 B2
(45) Date of Patent: Feb. 19, 2019

(54) METHOD AND APPARATUS FOR AUTOMATICALLY TESTING HIGH PRESSURE AND HIGH TEMPERATURE SEDIMENTATION OF SLURRIES

(71) Applicant: Halliburton Energy Services, Inc., Houston, TX (US)

(72) Inventors: Dale E. Jamison, Humble, TX (US); Robert J. Murphy, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 105 days.

(21) Appl. No.: 15/096,469

(22) Filed: Apr. 12, 2016

(65) Prior Publication Data

US 2016/0238504 A1 Aug. 18, 2016

Related U.S. Application Data

(62) Division of application No. 13/478,974, filed on May 23, 2012, now Pat. No. 9,341,556.

(51) Int. Cl.
| | |
|---|---|
| *G01N 9/32* | (2006.01) |
| *G01N 9/00* | (2006.01) |
| *G01N 15/04* | (2006.01) |
| *E21B 41/00* | (2006.01) |

(52) U.S. Cl.
CPC .............. *G01N 9/32* (2013.01); *E21B 41/00* (2013.01); *G01N 9/00* (2013.01); *G01N 15/04* (2013.01)

(58) Field of Classification Search
CPC .............. G01N 15/04; G01N 9/00; G01N 9/32
See application file for complete search history.

(56) References Cited

U.S. PATENT DOCUMENTS

| | | | |
|---|---|---|---|
| 2,845,793 A | 8/1958 | Cardwell, Jr. | |
| 4,194,391 A | 3/1980 | Rosenberger | |
| 4,313,340 A | 2/1982 | Schniewind | |
| 4,694,692 A * | 9/1987 | Brown ...................... | G01N 9/28 73/152.22 |
| 4,708,018 A * | 11/1987 | Brown ...................... | G01N 9/28 73/439 |
| 4,779,462 A | 10/1988 | Boullet et al. | |
| 4,924,695 A * | 5/1990 | Kolpak ................... | G01N 22/00 73/19.01 |

(Continued)

OTHER PUBLICATIONS

Schlumberger Oilfield Glossary, Sag Definition, web-based document, 2018.*

(Continued)

*Primary Examiner* — John Fitzgerald
(74) *Attorney, Agent, or Firm* — Tenley Krueger; Baker Botts L.L.P.

(57) ABSTRACT

A method and apparatus for automatically testing high pressure and high temperature sedimentation of slurries is described. The method includes pumping a sample drilling fluid into a test cell. The sample drilling fluid may be subjected to a pre-determined pressure and a pre-determined temperature for a pre-determined period of time. The test cell may also be oriented at non-vertical angle. The sample drilling fluid may be pumped out of the test cell and the density of the sample drilling fluid automatically measured relative to a displaced fluid volume of the sample drilling fluid.

7 Claims, 6 Drawing Sheets

(56) References Cited

U.S. PATENT DOCUMENTS

| | | | |
|---|---|---|---|
| 5,086,646 A | 2/1992 | Jamison et al. | |
| 5,233,863 A * | 8/1993 | Surjaatmadja | E21B 49/02 73/239 |
| 5,939,622 A * | 8/1999 | Fay | G01F 23/296 73/61.63 |
| 5,987,969 A | 11/1999 | Joseph et al. | |
| 6,176,323 B1 | 1/2001 | Weirich et al. | |
| 6,330,826 B1 | 12/2001 | Meeten | |
| 6,584,833 B1 | 7/2003 | Jamison et al. | |
| 6,612,156 B1 * | 9/2003 | Hakimuddin | B01F 3/1242 73/597 |
| 7,140,239 B2 * | 11/2006 | Greenwood | G01N 15/04 73/61.63 |
| 7,581,435 B2 * | 9/2009 | Pelletier | G01N 11/04 73/54.02 |
| 7,845,212 B1 | 12/2010 | Bi | |
| 7,870,782 B2 * | 1/2011 | Tehrani | G01N 15/06 73/152.07 |
| 7,894,991 B2 * | 2/2011 | Del Castillo | E21B 43/00 166/250.01 |
| 7,900,504 B2 | 3/2011 | Huynh | |
| 8,322,198 B2 | 12/2012 | Iverson et al. | |
| 8,573,048 B2 | 11/2013 | Slater | |
| 8,752,414 B2 | 6/2014 | Jamison et al. | |
| 9,341,556 B2 * | 5/2016 | Jamison | G01N 9/00 |
| 2004/0182138 A1 * | 9/2004 | Greenwood | G01N 15/04 73/53.03 |
| 2006/0070426 A1 * | 4/2006 | Pelletier | G01N 11/04 73/54.02 |
| 2007/0151763 A1 * | 7/2007 | Reitsma | E21B 21/08 175/48 |
| 2008/0236253 A1 | 10/2008 | Tehrani et al. | |
| 2008/0236891 A1 | 10/2008 | Huynh et al. | |
| 2009/0188312 A1 * | 7/2009 | Sears | C09K 8/42 73/152.22 |
| 2010/0042458 A1 * | 2/2010 | Rashid | E21B 43/122 703/10 |
| 2010/0139914 A1 * | 6/2010 | Tehrani | G01N 1/34 166/250.17 |
| 2011/0005832 A1 * | 1/2011 | McDonald | E21B 21/065 175/5 |
| 2011/0130965 A1 | 6/2011 | Slater et al. | |
| 2011/0167901 A1 | 7/2011 | Jamison et al. | |
| 2013/0139572 A1 | 6/2013 | Jamison et al. | |
| 2013/0139583 A1 | 6/2013 | Jamison et al. | |
| 2013/0186197 A1 | 7/2013 | Jamison et al. | |

OTHER PUBLICATIONS

International Preliminary Report on Patentability issued in related PCT Application No. PCT/US2013/041670, dated Dec. 4, 2014, 7 pages.

International Search Report and Written Opinion issued in related PCT Application No. PCT/US2013/041670, dated Sep. 9, 2013, 10 pages.

* cited by examiner

METHOD AND APPARATUS FOR AUTOMATICALLY TESTING HIGH PRESSURE AND HIGH TEMPERATURE SEDIMENTATION OF SLURRIES

CROSS-REFERENCE TO RELATED APPLICATION

This application is a divisional application of U.S. application Ser. No. 13/478,974, entitled "A METHOD AND APPARATUS FOR AUTOMATICALLY TESTING HIGH PRESSURE AND HIGH TEMPERATURE SEDIMENTATION OF SLURRIES" and filed on May 23, 2012, which is hereby incorporated by reference in its entirety.

BACKGROUND

The present disclosure relates generally to simulating downhole formation environments and, more particularly, the present disclosure relates to a method and apparatus for automatically testing high pressure and high temperature sedimentation of slurries.

Subterranean drilling operations typically utilize drilling fluids to provide hydrostatic pressure to prevent formation fluids from entering into the well bore, to keep the drill bit cool and clean during drilling, to carry out drill cuttings, and to suspend the drill cuttings while drilling is paused and when the drilling assembly is brought in and out of the borehole. In certain drilling fluids, fine solids may be mixed into a slurry with a liquid component. The slurry may then be introduced downhole as part of the drilling process. The effectiveness of the slurry may depend, however, on the static sag property of the drilling fluid, which describes the tendency of a fine solid, such as barite, calcium carbonate, etc., to separate from the liquid component and settle. The static sag can result in variations in mud density in the wellbore, with the light density on top and the heavy density is at the bottom.

Tests to determine the static sag property of a drilling fluid typically are performed manually and generate limited density profiles. For example, current systems may use a syringe to manually draw a sample(s) from a particular area(s) of a test container, which limits the density measurement to the particular areas where the sample(s) were collected. Another test system uses a cup at a bottom of a test container to collect settled solids, which are then weighed to obtain a density, but such a method does not provide density measurements at particular locations within the drilling fluid. Moreover, the structural components of existing test apparatuses limit the pressures which can be applied to the drilling fluids, which, in turn, limits the types of subterranean formation which can be simulated. What is needed is an automated and robust way to test static sag of drilling fluids in a variety of simulated conditions.

FIGURES

Some specific exemplary embodiments of the disclosure may be understood by referring, in part, to the following description and the accompanying drawings.

FIGS. 1a-b illustrate an example test cell, incorporating aspects of the present disclosure.

FIGS. 2a-c illustrate an apparatus and method automatically testing sag properties of drilling fluids, according to aspects of the present disclosure.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to simulating downhole formation environments and, more particularly, the present disclosure relates to a method and apparatus for automatically testing high pressure and high temperature sedimentation of slurries.

Illustrative embodiments of the present disclosure are described in detail herein. In the interest of clarity, not all features of an actual implementation may be described in this specification. It will of course be appreciated that in the development of any such actual embodiment, numerous implementation-specific decisions must be made to achieve the specific implementation goals, which will vary from one implementation to another. Moreover, it will be appreciated that such a development effort might be complex and time-consuming, but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the disclosure. Embodiments of the present disclosure may be applicable to horizontal, vertical, deviated, or otherwise nonlinear wellbores in any type of subterranean formation. Embodiments may be applicable to injection wells as well as production wells, including hydrocarbon wells.

The present disclosure describes a system and apparatus for automatically testing sag properties of drilling fluids. The apparatus, for example, may include a test cell with a first pump and a second pump in fluid communication with the test cell. The first pump may automatically introduce a sample drilling fluid into the test cell, and the second pump may automatically impart a pre-determined pressure on the sample drilling fluid within the test cell. A density transducer may also be in fluid communication with the test cell, and may be operable to automatically measure a density of the sample drilling fluid relative to a fluid volume of the sample drilling fluid, providing a complete or near complete, top-to-bottom density profile of the drilling fluid.

Figure 1A:
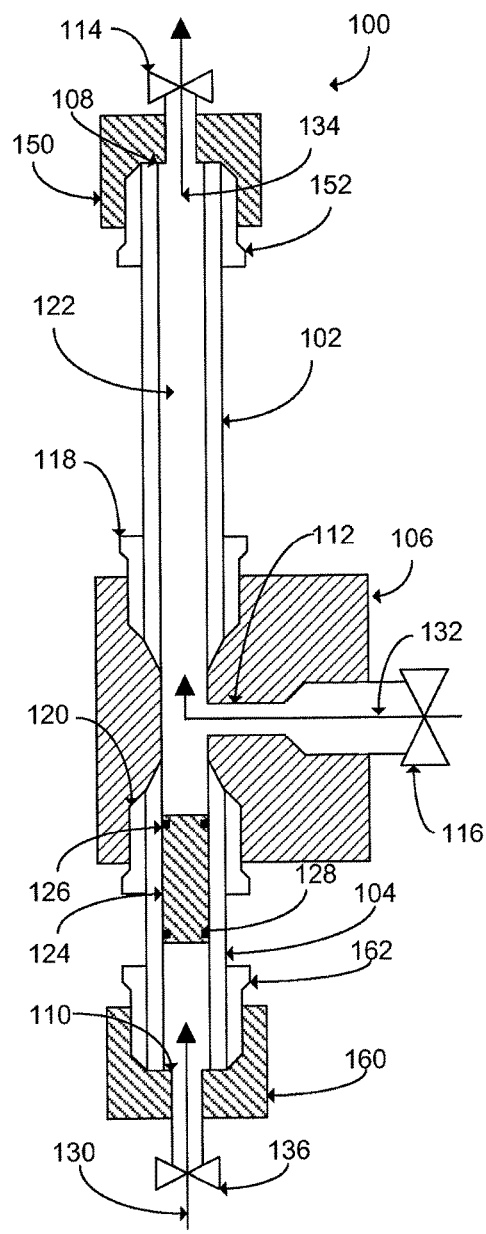
Figure 1B:
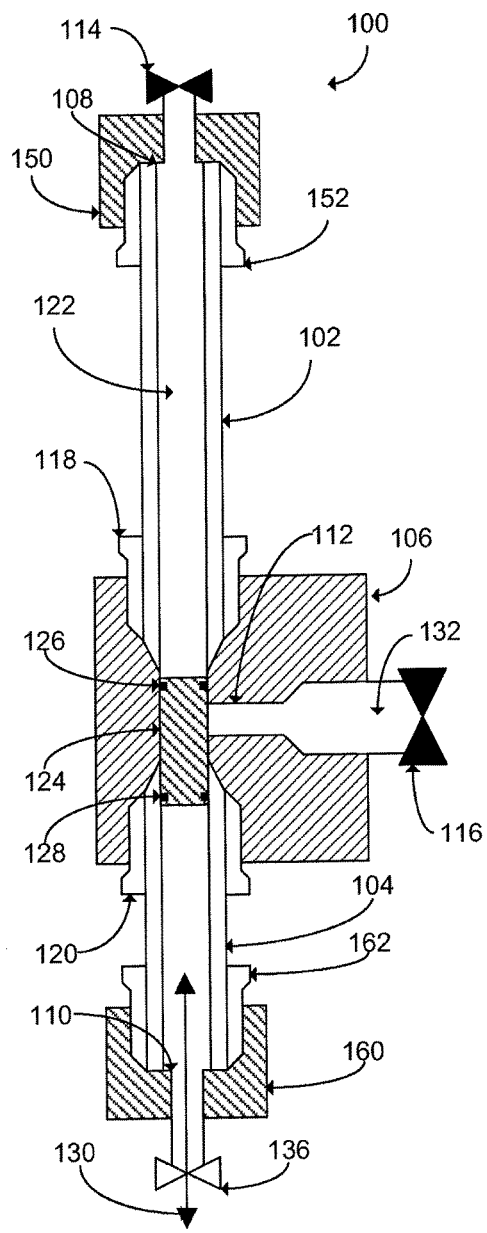

FIGS. 1a-b illustrate an example test cell 100, according to aspects of the present disclosure. Test cell 100 may comprises a generally cylindrical, tubular structure comprising a first tubular portion 102, a second tubular portion 104, and a tee fitting 106. The tee fitting 106 may be disposed between the first tubular portion 102 and second tubular portion 104. The first tubular portion 102, a second tubular portion 104, and a tee fitting 106 may define a single test chamber 122 with a generally consistent inner diameter. In certain embodiments, the first tubular portion 102 and the second tubular portion 104 may comprise standard one inch outside diameter pressure tubing, rated to withstand 20,000 pounds per square inch (psi) or more. The test chamber 122, within the test cell 100, may have, for example, a 0.562 inch inner diameter and a length of 19 inches long. Although the test cell 100 and its illustrated components are shown as cylindrical, with resulting diameters, other shapes and sizes are possible, as would be appreciated by one of ordinary skill in view of this disclosure.

The first tubular portion 102 and second tubular portion 104 may be integral with or coupled to the tee fitting 106 via high-pressure fittings 118 and 120. Like the first tubular portion 102 and the second tubular portion 104, the high-pressure fitting 118 and 120 may be rated to withstand up to 20,000 psi. Each of the first tubular portion 102, the second tubular portion 104, and the tee fitting 106 may have a similar internal diameter, or may be modified to equalize their internal diameters. For example, tee fitting 106 may include a sleeve that equalizes the internal diameter of the tee fitting with the internal diameters of the first tubular portion 102 and the second tubular portion 104, such that the test chamber 122 comprises a generally consistent diameter.

The test cell 100 may further include an isolator, isolation piston 124, within the test chamber 122. Isolation piston 124 may have an outer diameter similar to diameter of the inner chamber 122, and may move from the bottom of the test cell to the top of the test cell, within the test chamber 122. As can be seen, the isolation piston 124 may include seals 126 and 128 that isolate the area of the test cell 100 below the isolation piston 124 from the area above the isolation piston 124. In certain embodiments, seals 126 and 128 may comprise o-rings installed within grooves on the isolation piston 124 and may engage with the wall of the test cell 102 defining the test chamber 122 as it moves within the test chamber 122. The seals 126 and 128 may be separated on the isolation piston 124 by a pre-determined distance, such that as the isolation piston 124 moves through the tee fitting 106, one seal remains in contact with the wall of the test chamber 122 which the other seal is passing port 112, as will be described below.

The test cell 100 may include multiple openings, providing multiple fluid communication channels with the test chamber 122. In certain embodiments, the first tubular portion 102 may define a first opening 108 at the top of the test cell 100, the second tubular portion 104 may define a second opening 110 at the bottom of the test cell 100, and the tee fitting may define a third opening 112, a side port between the first opening 108 and the second opening 110. Each of the openings may provide fluid communication with the inner chamber 122. In operation, the test cell 100 may be coupled to and in fluid communication with other elements through first opening 108, second opening 110, and side port 112 via control valves 114, 136, and 116, respectively. Each of the control valves may be controlled automatically as part of an automated control system, as will be described below.

In certain embodiments, such as the embodiment shown in FIGS. 1a and 1b, the top and bottom of the test cell 100 may be coupled to high-pressure rated connections. For example the top of the test cell may be coupled to connection 150 via high-pressure fitting 152, and the bottom of the test cell 100 may be coupled to connection 160 via high-pressure fitting 162. The high-pressure rated fitting 152 and 162 may be rated to handle pressures similar to the fittings 118 and 120 described previously.

FIG. 1a illustrates an example configuration whereby the test cell 100 is prepared for testing. In certain embodiments, a sample drilling fluid may be pumped into the test chamber 122 through side port 112 via open control valve 116, as indicated by arrow 132. As can be seen, the sample drilling fluid may be contained within the test chamber 122 on a top side of the isolation piston 124 proximate the first opening 108, separated from the bottom part of the test chamber 122, proximate the second opening 110. As the sample drilling fluid enters the test chamber 122, air within the test chamber may be forced out of first opening 108 through open control valve 114, as indicated by arrow 134. Once the portion of the test chamber 112 above the isolation piston 124 is filled with the sample drilling fluid, and the control valve 114 closed to isolate the sample drilling fluid, a pressurization fluid may also be pumped into the test chamber 122 through the second opening 110 via open control valve 136, as indicated by arrow 130. Notably the pressurization fluid may be isolated from the sample drilling fluid by the isolation piston 124.

Once the air is forced out of the test chamber 122, control valves 114 and 116 may be closed, isolating the sample drilling fluid within a top portion of the test chamber 122, as is shown in FIG. 1b. Pressurization fluid can then be forced into or removed from the lower portion through the second opening 110, imparting pressure on the sample drilling fluid by imparting pressure on the isolation piston 124. The pressure may be applied to the sample drilling fluid for a pre-determined period of time, at which time the control valve 114 may be opened. Once the control valve 114 is opened, additional pressurization fluid may be introduced into the test chamber 122 through the second opening 110, forcing the isolation piston upwards and the sample drilling fluid out of the top opening 108. Additional pressurization fluid may be added into the test chamber 122 until the isolation piston 124 contacts a top surface of the test cell 100. At that point, the pressure within the test chamber may spike, triggering the removal of the pressurization fluid from the test chamber 122.

Figure 2A:
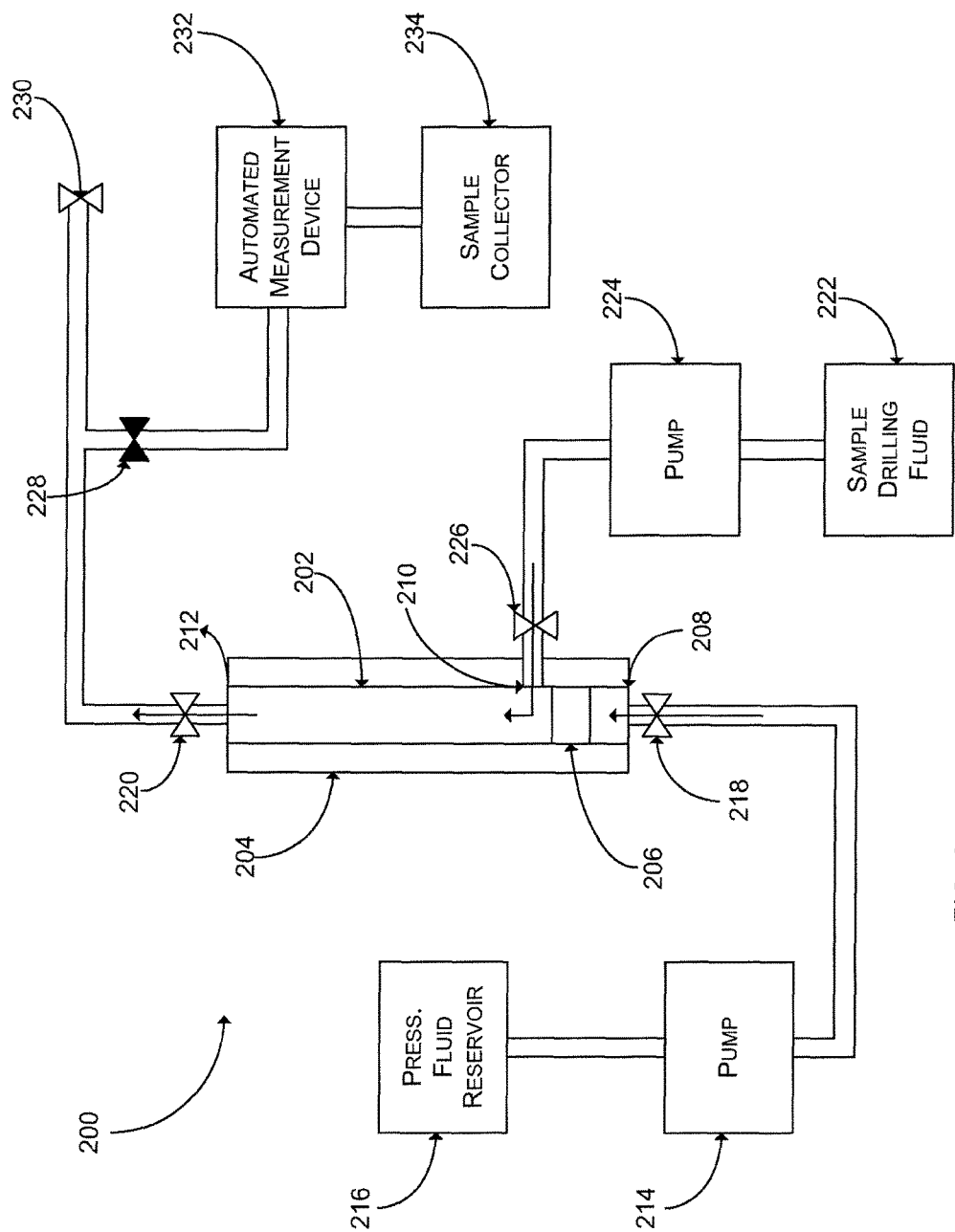
Figure 2B:
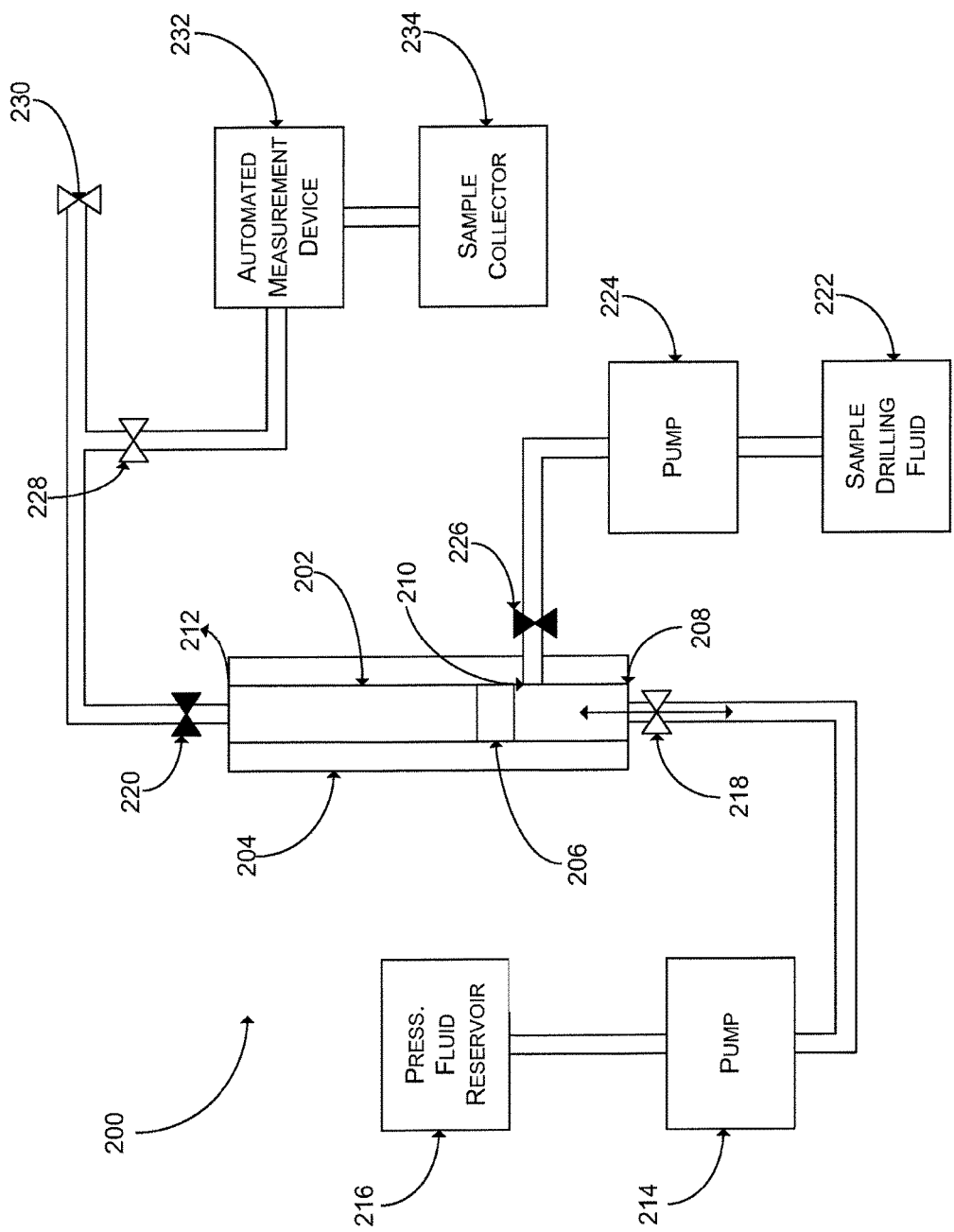
Figure 2C:
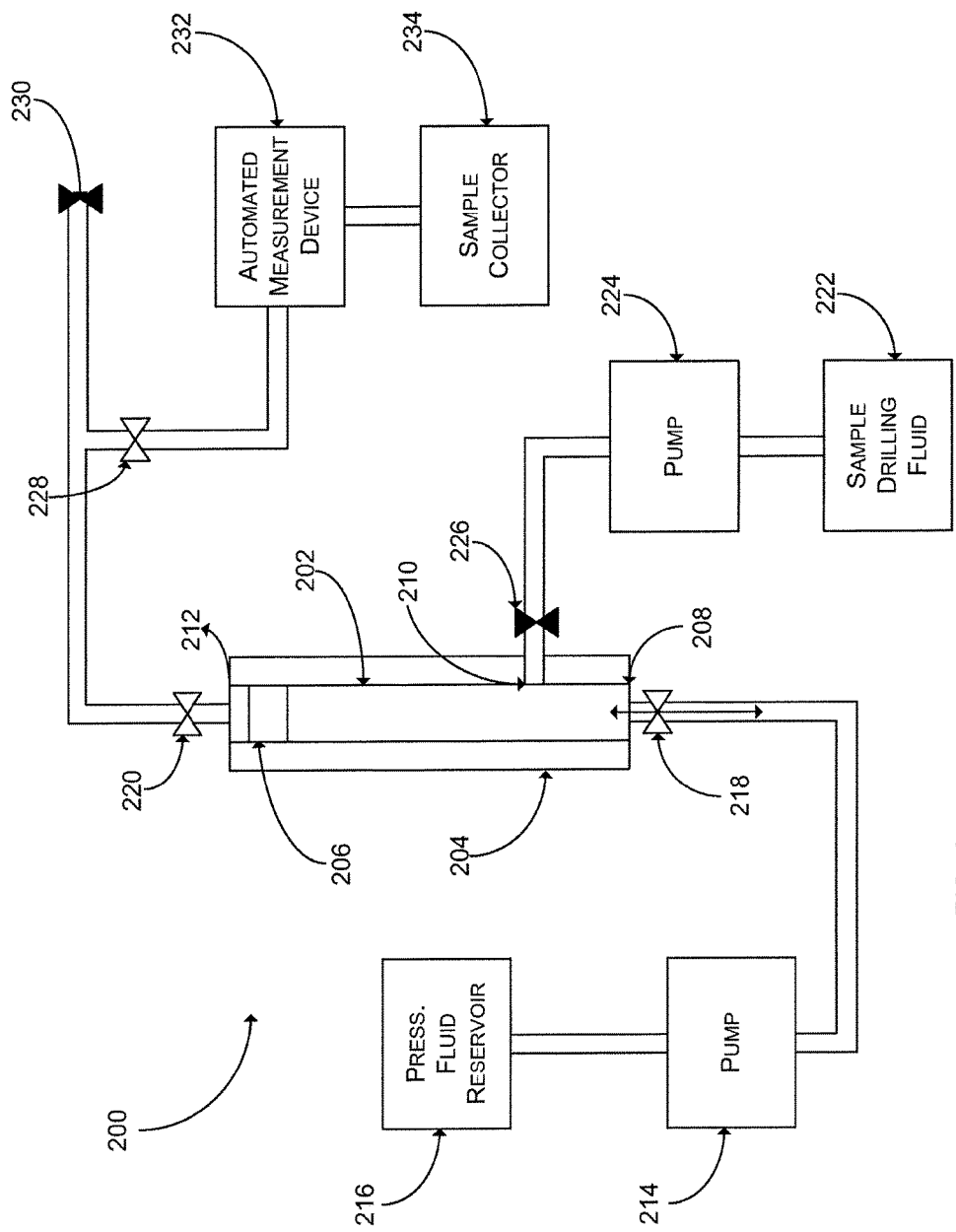

FIGS. 2a-c show an example testing apparatus 200 incorporating the test cell 202, according to aspects of the present inventions. Test cell 202 may be disposed within a heating jacket 204. The heating jacket 204 may comprise a single element at least partially surrounding the test cell 202, or may be segmented. The heating jacket 204 may impart heat to a sample drilling fluid disposed within the test cell 202, simulating subterranean conditions.

The test cell 202 may be in fluid communication with a first pump 224 through an opening, side port 210. The side port 210 may comprise an opening in a tee fitting, as described above with respect to FIGS. 1a and 1b. Additionally, the opening may not be disposed along the side of the test cell 202, but may be located elsewhere along the test cell 202 body. The first pump 224 may comprise a low pressure pump and may be in fluid communication with a sample drilling fluid reservoir 222.

The test cell 202 may also be in fluid communication with a second pump 214 through an opening 208 in the bottom of the test cell 202. In certain embodiments, as will be described below, the pump 214 may comprise a high-pressure pump, such as a syringe pump, that is operable to pump fluid into and out of the test cell 202. The second pump 214 may be in fluid communication with a pressurization fluid reservoir 216.

The test cell 202 may be in further communication with an automated measurement device 232 through opening 212 at the top of the test cell 202. In certain embodiments, the automated measurement device may comprise a density transducer, that is operable to receive a sample drilling fluid from the test cell 202 and determine the density of the fluid relative to the fluid volume displaced within the test cell 202, as will be described below. The automated measurement device 232 may be in fluid communication with a sample collector 234, which may collect the sample drilling fluid once it passes through the automated measurement device 232. In other embodiments, the automated measurement device 232 may be excluded from the apparatus. In those embodiments, for example, fluid volumes can be pumped incrementally from the test cell 202. The density of the sample drilling fluid from the test cell 202 may be determined relative to the fluid volume displaced within the test cell 202 by determining the mass of the sample drilling fluid for each incremental volume sample.

FIG. 2a illustrates an example apparatus configuration whereby the test cell 202 is being filled with a sample drilling fluid and prepared for testing. As can be seen, the control valve 226 between the first pump 224 and the test cell 202 may be open, allowing the sample drilling fluid from the sample drilling fluid reservoir 222 to be pumped into the test cell 202 in the area above the isolation piston 206. The control valve 218 between the second pump 214 and the test cell 202 may further be open, allowing the pressurization fluid from the pressurization reservoir to be pumped into the test cell 202 in the area below the isolation piston. In certain embodiments, enough pressurization fluid may be pumped into the test cell 202 to ensure that the isolation piston is essentially stationary which the first pump 224 pumps the sample drilling fluid into the test cell 202. In other embodiment, control valve 218 may be shut to ensure that the isolation piston remains stationary. The volume under the isolation piston 206 may be pre-filled with pressurization fluid. As the test cell 202 is filled with the sample drilling fluid, the air within the test cell 202 will be flushed out of the test cell, through open control valves 220 and 230. During the filling process, control valve 228 may be closed, isolating the automated measurement device 232.

Once the air has been flushed out of the test cell 202, control valves 220 and 226 may be closed, isolating the sample drilling fluid within the test cell 202, as can be seen in FIG. 2b. Once the sample drilling fluid is isolated within the test cell 202, a pre-determined pressure and a pre-determined temperature may be applied to the sample drilling fluid. For example, the heating jacket 204 may then begin heating the sample drilling fluid to a pre-determined temperature corresponding to simulated subterranean conditions. Additionally, the second pump 214 may be engaged to apply a pressure to the sample drilling fluid by pumping additional pressurization fluid into the test cell 202, below the isolation piston 206. As can be seen, the isolation piston 206 may be forced upward by the pressurization fluid to apply the target pressure on the sample drilling fluid. As the temperature increases, the sample drilling fluid may expand, increasing the pressure within the test cell beyond the target pressure. In certain embodiments, the second pump 214 may monitor the pressure within with test cell 202 and remove some pressurization fluid from the test cell 202 to return the test cell 202 to the target pressure. The pre-determined temperature and pre-determined pressure may be selected to correspond to subterranean conditions in which a similar drilling fluid may be used.

In certain embodiments, the test cell 202 may be also oriented at a pre-determined, non-vertical angle, such as up to 60°. By orienting the test cell 202 at a non-vertical angle, the apparatus 200 can be used to simulate a non-vertical borehole, increasing the subterranean conditions that can be simulated as part of the sag measurement process. The test cell 202 may remain at the pre-determined temperature, pre-determined pressure, and the pre-determined orientation for a particular period of time, such as 8 to 96 hours. The time period for the test may be selected according to static time a similar drilling fluid might be exposed to in actual downhole use. After the pre-determined time period, the test cell 202 may be cooled to, for example, 120° F. to allow for the test cell to be exposed to atmospheric pressure.

FIG. 2c illustrates an example measurement configuration for the apparatus 200. Once the sample drilling fluid in test cell 202 has been exposed to the downhole pressures and temperatures as part of the testing process, the sample drilling fluid may be pumped out of the test cell 202, and the density of the sample drilling fluid may be automatically measured relative to a displaced fluid volume of the sample drilling fluid. For example, control valve 220 may be opened to allow the sample drilling fluid to pumped out of the test cell 202. Additionally, control valve 228 may be opened and control valve 230 may be closed, forcing the sample drilling fluid to be pumped into the automated measurement device 232.

Second pump 214 may pump pressurization fluid into the test cell 202. Pumping the pressurization fluid into the test cell 202 will force the isolation piston 206 upwards, causing the sample drilling fluid to be pumped out of the test cell 202. As the sample drilling fluid is received in the automated measurement device 232, the automated measurement device 202 may take continuous, or near continuous, measurements of the density of the sample drilling fluid. In certain embodiments, the density of the sample drilling fluid may be determined relative to the sample drilling fluid's location within the test cell 202. The sample drilling fluid's location within the test cell may be based, at least in part, on the volume of the sample drilling fluid that has been displaced from the test cell 202 at the time the measurement is taken. In certain embodiments, the amount of displaced drilling fluid may correspond to the amount of pressurization fluid that has been pumped into the test cell 202 by the second pump 214 to displace the sample drilling fluid within the test cell 202.

Figure 4:
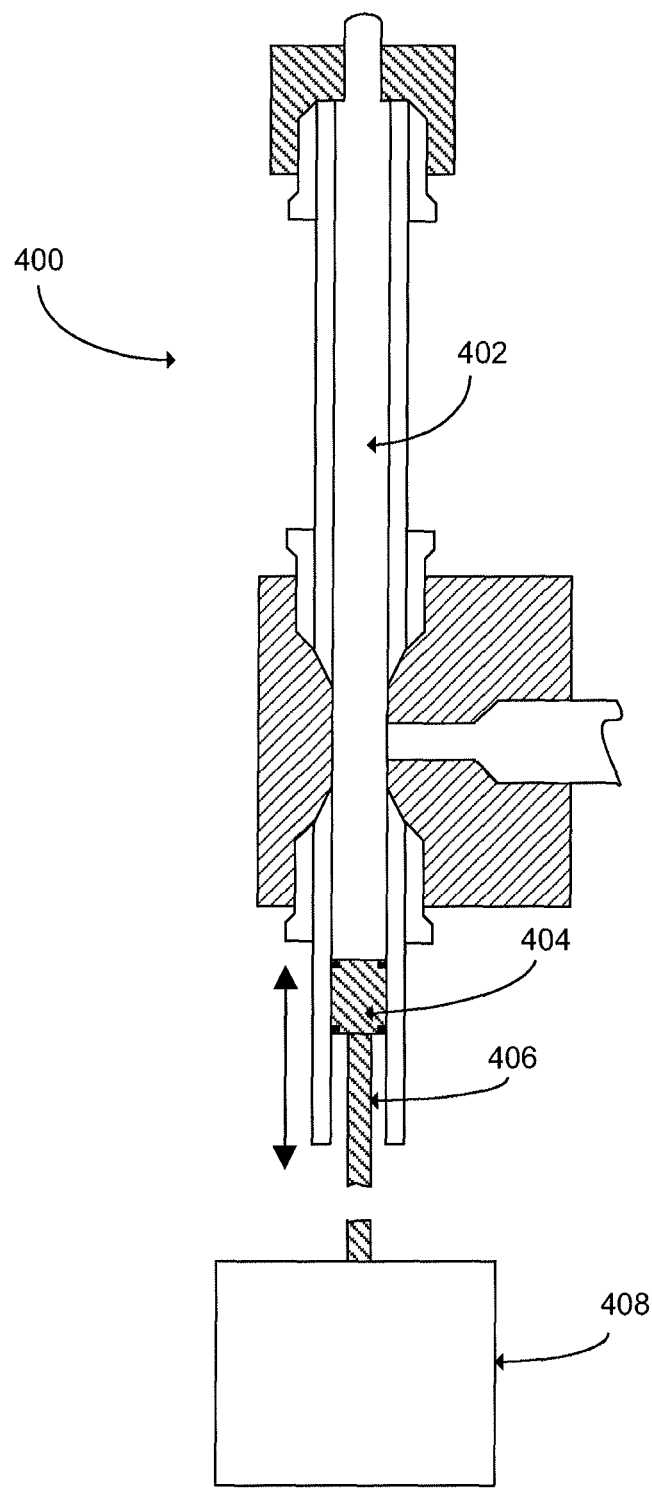
FIG. 4 illustrates an example test cell, incorporating aspects of the present disclosure.

Although the embodiments described above include a test cell with an internal isolation piston, other embodiments of the apparatus are possible for subjecting the sample drilling fluid to a pre-determined pressure. FIG. 4 illustrates an example test cell 400 that includes a plunger 404 instead of an isolation piston. In certain embodiment, the plunger 404 may comprise a syringe-pump-like plunger or piston that can be used to impart a pre-determined pressure directly on the sample drilling fluid within the test chamber 402. The plunger 404 may be coupled to a shaft 406, which is in turn coupled to plunger driver 408 that may move the plunger 404 into and out of the test chamber 402, imparting pressure on the sample drilling fluid within the test chamber 402. Likewise, the plunger 404 could be fully inserted to eject the sample drilling fluid or retracted to allow a particular volume of sample drilling fluid to be pumped into the test chamber 402. The test cell 400 could, in certain embodiments, be substituted for the test cell shown in FIGS. 2a-c, eliminating the need for the pressurization fluid reservoir 216 and pump 214.

Figure 3:
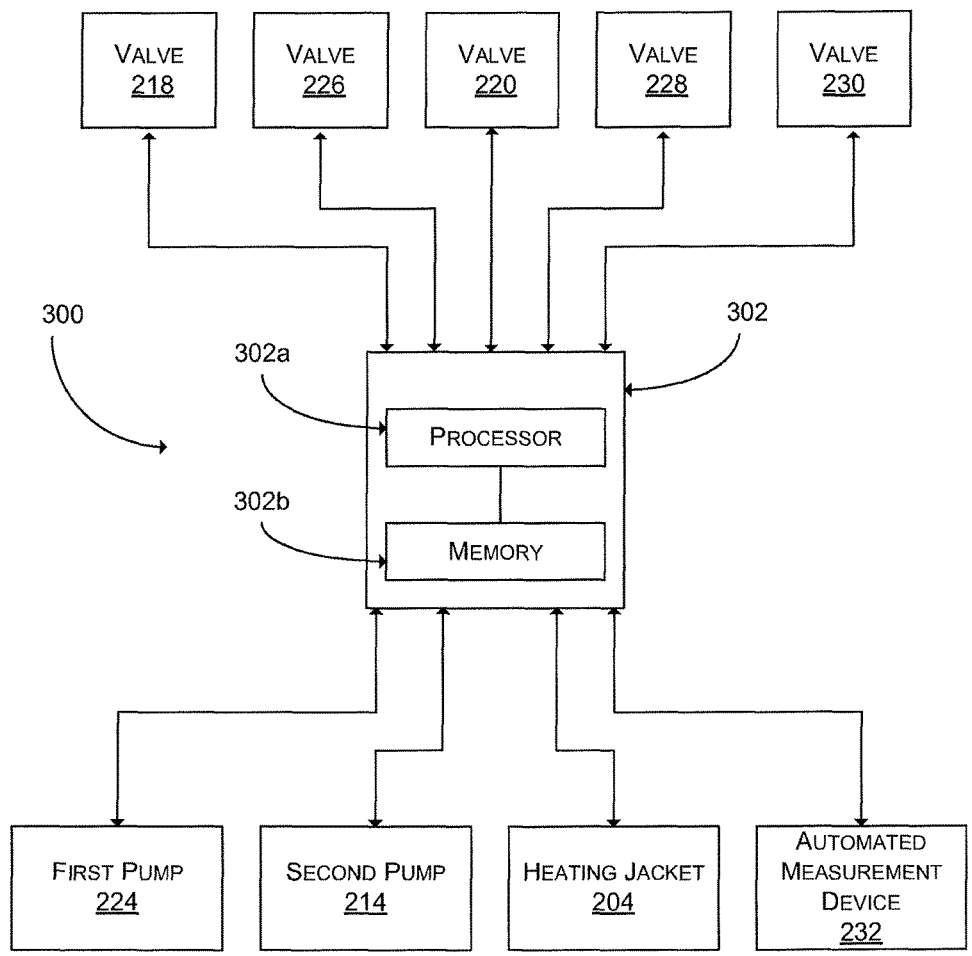
FIG. 3 illustrates an example automated control system, according to aspects of the present disclosure.

As would be appreciated by one of ordinary skill in view of this disclosure, the apparatus 200 illustrated in FIGS. 2a-c may be advantageous because many of the components and steps my be automated. For example, the steps of filling the test cell with a sample drilling fluid, subjecting the sample drilling fluid to the simulated downhole conditions, and measuring the sag profile of the sample drilling fluid may all be automated. In certain embodiments, some or all of the control and measurement described above may be performed using an automated control system 500, as illustrated in FIG. 3. In certain embodiments, the automated control system 300 may comprise a Supervisory Control and Data Acquisition (SCADA) system.

As can be seen, the automated control system 300 may include a control unit 302, such as a computer system, that includes a processor 302a and memory coupled to the processor 302b. The control unit may be electrically or communicably coupled, via wires or other suitable transmission media, to elements of the apparatus described above. For example, the control unit 302 may be in communication with and issue commands to control valve 218, 226, 220, 228, and 230 causing them to open or close automatically depending on the corresponding steps of the sag measurement process. Likewise, the control unit 302 may be in communication with and issue commands causing the first pump 224 and second pump 214 to pump the corresponding fluids into the test cell, including the rate with which the fluid are pumped into the test cell, and in the case of the second pump 214. Additionally, the control unit may include saved parameters corresponding to the pre-determine temperature, pre-determined pressure, pre-determined orientation, and pre-determined time described above. For example, the control unit 302 may be cause the heating jacket 204 to heat the sample drilling fluid to the pre-determined temperature. Likewise, the control unit 302 may cause the test cell to be oriented at a particular non-vertical angle, and cause the second pump 214 to impart and maintain a target pressure on the sample drilling fluid. Likewise, the control unit may automatically switch between downhole simulation and measurement mode, opening up the appropriate control valves and triggering the automated measurement device 232 to begin measuring the sag properties of the sample drilling fluid. The control unit may also receive the measurements from the automated control device 232, process the data, and generate information related to the sag properties of the sample drilling fluid.

Although the test cell described above is shown in a substantially vertical configuration with a corresponding top opening, side opening, and bottom opening, such a configuration is not meant to be limiting. Rather, the test cell may be oriented in a variety of ways as would be appreciated by one of ordinary skill in view of this disclosure. For example, the test cell may be inverted such that the pressurization fluid is pumped into the test cell through a top opening and the sample drilling fluid pumped into the test cell through a bottom opening.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that it introduces.

What is claimed is:

1. A method for testing a property of drilling fluids, comprising:
    pumping a sample drilling fluid into a test cell through a first control valve by a first pump in fluid communication with the test cell;
    isolating the sample drilling fluid within the test cell by the first control valve and a second control valve;
    subjecting the sample drilling fluid within the test cell to a pre-determined pressure and a pre-determined temperature for a pre-determined period of time by opening a third control valve to allow a pressurization fluid to be pumped into the test cell by a second pump in fluid communication with the test cell when the sample drilling fluid is isolated within the test cell by the first control valve and the second control valve;
    pumping the sample drilling fluid out of the test cell through the second control valve; and
    measuring a density of the sample drilling fluid displaced from the test cell through the second control valve by a density transducer in fluid communication with the test cell.

2. The method of claim 1, wherein pumping the sample drilling fluid into the test cell comprises pumping by the first pump the sample drilling fluid through a side port of the test cell.

3. The method of claim 1, further comprising the step of orienting the test cell at a pre-determined, non-vertical angle.

4. The method of claim 1, wherein subjecting the sample drilling fluid within the test cell to a pre-determined pressure includes moving a plunger within the test cell.

5. The method of claim 4, wherein subjecting the sample drilling fluid within the test cell to a pre-determined temperature includes heating the test cell to a pre-determined temperature using a heating jacket at least partially surrounding the test cell.

6. The method of claim 5, wherein the heating jacket is at least partially controlled by an automated control system.

7. The method of claim 6, wherein the automated control system comprises a Supervisory Control and Data Acquisition (SCADA) system.

* * * * *